United States Patent [19]

Palomo Coll

[11] Patent Number: 5,232,706
[45] Date of Patent: Aug. 3, 1993

[54] ORAL PHARMACEUTICAL PREPARATION CONTAINING OMEPRAZOL

[75] Inventor: Alberto Palomo Coll, Barcelona, Spain

[73] Assignees: Esteve Quimica, S.A.; Centro Genesis Para La Investigacion, S.L., both of Barcelona, Spain

[21] Appl. No.: 805,878

[22] Filed: Dec. 9, 1991

[30] Foreign Application Priority Data

Dec. 31, 1990 [ES] Spain .................................. 9100167
Jun. 24, 1991 [ES] Spain .................................. 9101493

[51] Int. Cl.⁵ ...................... A61K 9/30; A61K 31/415; A61K 31/155; A61K 31/135
[52] U.S. Cl. ................................. 424/475; 424/494; 424/495; 514/394; 514/395; 514/632; 514/653
[58] Field of Search ....................... 424/475, 494, 495; 514/394, 395, 653, 632

[56] References Cited

U.S. PATENT DOCUMENTS 4,786,505 11/1988 Lovgren et al. .................... 424/475

FOREIGN PATENT DOCUMENTS 0444625 9/1991 European Pat. Off. .

OTHER PUBLICATIONS

Chemical Abstracts, (110:225311s), 1989.

Primary Examiner—Frederick E. Waddell
Assistant Examiner—K. Weddington
Attorney, Agent, or Firm—Bell, Seltzer, Park & Gibson

[57] ABSTRACT

The preparation comprises a nucleus formed by a mixture of omeprazol or an alkali salt of omeprazol with a first basic compound; the nucleus has two coatings, the first of which is formed by one or more layers formed by a basic water soluble excipient and by a second basic compound, while the second coating is formed by an enteric coating.

11 Claims, No Drawings

ORAL PHARMACEUTICAL PREPARATION CONTAINING OMEPRAZOL

BACKGROUND OF THE INVENTION

1. Field of the Invention

The invention relates to an oral pharmaceutical preparation containing omeprazol, the chemical name of which is 5-methoxy-2-(((3,5-dimethyl-4-methoxy-2-pyridinyl)methyl)sulfinyl)-1H-benzimidazole, of formula:

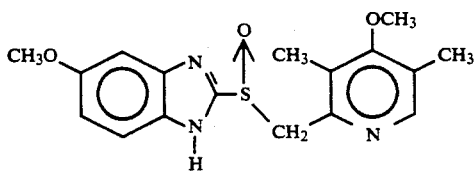

or an alkali salt thereof.

2. Reference to the Prior Art

The synthesis of these compounds is disclosed by the present inventor in Spanish patents nos 9002764, 9003113 and 9003174.

Omeprazol is a very effective drug for the treatment of gastric and duodenal ulcers.

Omeprazol is stable at basic pH, but rapidly decomposes at neutral or acid pH. Likewise, moisture has a negative effect on the stability of the compound. Therefore, if omeprazol is administered orally, it must be protected from the gastric juices, which are acid, so that it may reach the small intestine where it is absorbed, in unaltered state (GB-2,189,698-A).

This protection is achieved by covering the omeprazol nucleus with an enteric coating, insoluble in an acid medium but soluble or readily disintegratable in a neutral or basic medium. Nevertheless, the compounds regularly used for this purpose are acid, whereby the nucleus tends to discompose with time. (GB-2,189,698-A)

This problem is solved in part by increasing the basic response of the nucleus, either by introducing the omeprazol in alkali or alkali earth salt form, or by mixing the omeprazol with a basic compound, or by combining both possibilities. In this way a basic micro-pH is formed around the omeprazol particles, increasing the stability thereof, but it does not eliminate the contact of the omeprazol with the acid enteric coating.

The fact that the nucleus is basic causes a further problem. The outer layer is water permeable in part, so that after administration of the drug the water in the digestive channel could reach the nucleus and dissolve it in part. The alkaline solution thus formed would thereafter attack the enteric coating, finally causing premature destruction thereof.

These difficulties are overcome by interposing a first coating formed by one or more separation layers of an appropriate nature between the nucleus and the enteric coating. For the preparation of these layers there is used a compound or polymer used for film coating which is inert, water soluble and pharmacologically acceptable, for example sugar, polyethylene glycol or polyvinyl alcohol, possibly accompanied by a basic compound. This first or internal coating separates the omeprazol from the external acid coating. It furthermore has the secondary function of acting as a pH buffer zone, such that the stomach acidity may not penetrate to the nucleus and the basicity of the nucleus may not affect the enteric coating (GB-2, 189,698-A).

Of course, the basic compounds cited in the foregoing paragraphs must be physiologically acceptable. To be precise, for omeprazol, the literature cites the Na, K, Ca, Mg and Al salts of weak organic or inorganic acids, such as citric, phosphoric or carbonic acid and the oxides and hydroxides of Ca, Mg and Al (GB-2.189.698-A).

SUMMARY OF THE INVENTION

According to the invention, the oral pharmaceutical preparation containing omeprazol as active ingredient comprises: a) a nucleus containing omeprazol or an alkali salt of omeprazol mixed with a first basic compound; b) a first coating of at least one intermediate layer formed by an excipient and a second basic compound; and c) a second coating formed by an enteric coating.

The present invention describes the use of new physiologically acceptable basic compounds to achieve the necessary stabilization of the omeprazol in the nucleus and to isolate it more effectively from the external acidity.

To be precise, said basic compounds are sodium, potassium, magnesium, calcium, aluminum or dihydroxyaluminium salts of amino acids, such as glycocoll ($pKa_2=9.6$), glutamic acid ($pKa_3=9.67$) or lysine ($pKa_2=8.9$, $pKa_3=10.28$), or a pyridine carboxylic acid, such as nicotinic acid, or they are organic bases, such as guanidine ($pK=12.5$) or a salt of said bases with an weak organic or inorganic acid, for example guanidine carbonate, guanidine sodium carbonate, guanidine phosphate or guanidine disodium phosphate, or with an amino acid such as glycocoll or glutamic acid. The compound must, of course, be physiologically acceptable.

New research has led to new compounds which are also useful for the above purposes. These compounds are basic amino acids, i.e., amino acids whose structure contains more amino radicals than carboxylic acid groups. Outstanding among these are arginine, histidine, lysine and tryptophane.

Ranitidine, the chemical name of which is N-(2-(((5-((dimethylamino)methyl)-2-furanyl)methyl)thio)ethyl)-N'-methyl-2-nitro-1,1-ethenediamine, of formula II

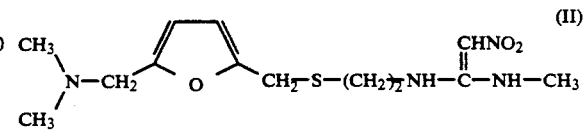

or famotidine, the chemical name of which is 3-(((2-((aminoiminomethyl)amino)-4-thiazolyl)methyl)thio)-N-(aminosulfonyl)-propanimidamide, of formula III

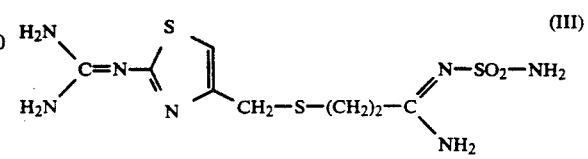

or a mixture of these products may also be used as basic compound for the nucleus. Both compounds are used, like omeprazol, for treating gastrointestinal ulcers.

The mixture of compounds of the nucleus is formulated as pellets, tablets or gelatine capsules by way of conventional pharmaceutical techniques.

The separation layer or layers are applied to the nuclei (pellets or tablets) by conventional coating techniques, using a solution of the excipient in water or in the regular organic solvents. As excipient there is used an inert water soluble compound or polymer used for film coatings, for example hydroxypropylmethylcellulose, hydroxypropylcellulose, polyvinyl alcohol, polvinylpyrrolidone or sugar. In the case of gelatine capsules, the capsule itself serves as separation layer.

Finally, the enteric layer is applied over the covered nuclei with one or more separation layers using solutions or suspensions of polymers normally used for this type of coating, for example cellulose acetate phthalate, hydroxypropylmethylcellulose phthalate, methacrylic acid and methyl methacrylate copolymer or polyvinyl acetate phthalate. Dispersing, colouring agents or pigments may be included in the enteric coating.

In turn, the process of the invention is characterized in that a member of a group of compounds formed by omeprazol and an alkaline omeprazol salt is mixed with a first basic compound, forming a nucleus which is given a first coating of at least one layer formed by an inert water soluble excipient and by a second basic compound, and a second coating formed by an enteric coating.

The excipient may be sugar or polyvinyl alcohol and the enteric coating is formed by an acid polymer such as cellulose phthalate.

Said basic compounds are aluminium or dihydroxyaluminium alkali or alkali earth salts of amino acids such as glycocoll or of a pyridine carboxylic acid such as nicotinic acid, or they are organic bases such as guanidine or a salt of said bases with a weak organic or inorganic acid or with an amino acid, for example guanidine disodium phosphate or guanidine glycocholate. These compounds must be physiologically acceptable.

As stated above, the basic compound of the nucleus may be ranitidine, famotidine or a mixture of these compounds.

EXAMPLE 1

5400 g of powdered mannitol, 260 g of anhydrous lactose, 200 g of hydroxypropylcellulose and 130 g of microcrystalline cellulose were mixed together and a suspension of 650 g of omeprazol, 17 g of lauryl sodium sulphate and 30 g of guanidine disodium phosphate in 1500 ml of water was added. The moist mass was stirred until it reached an appropriate consistency and was pressed in a pellet forming apparatus. The pellets were dried and were sorted in adequate particle sizes.

Then, 2000 g of the pellets were sprauved in a fluid bed apparatus with a spray formed by a solution of 80 g of hydroxypropylcellulose and 20 g of guanidine disodium phosphate in 1600 ml of water.

Finally, 150 g of pellets coated as described in the foregoing paragraph were sprayed in a fluid bed apparatus with a spray formed by a solution of 20 g of hydroxypropylmethylcellulose phthalate and 1 g of cetyl alcohol in a mixture of 180 g of acetone and 80 g of ethanol.

The pellets were dried to a moisture content of about 0.5%, they were sorted in sizes and were encapsulated in gelatine together with a dehydrating compound.

EXAMPLE 2

The procedure of Example 1 was followed, but using 16 g of L-lysine instead of the said 20 g of guanidine disodium phosphate.

What is claimed is:

1. An oral pharmaceutical preparation containing omeprazol, as active ingredient which comprises:
   (a) a nucleus formed by a mixture of a first basic organic compound and a compound selected from the group consisting of omeprazol and an alkali salt of omeprazol;
   (b) a first coating of said nucleus comprising at least one layer of a basic water soluble excipient and a second basic organic compound; and
   (c) a second coating formed by an enteric coating.

2. The preparation of claim 1, wherein said alkali salt of omeprazol is the sodium, potassium or lithium salt thereof.

3. The preparation of claim 1, wherein said first basic compound of the nucleus is either ranitidine, the chemical name of which is N-(2-(((5-((dimethylamino)methyl)-2-furanyl)methyl)thio)ethyl)-N'-methyl-2-nitro-1,1-ethenediamine, or famotidine, the chemical name of which is 3-(((2-((aminoiminomethyl)amino)-4-thiazolyl)methyl)thio)-N-(aminosulfonyl)-propanimidamide, or mixtures thereof.

4. A process for producing an oral pharmaceutical preparation comprising omeprazol as active ingredient which comprises:
   (a) preparing a nucleus formed by a mixture of a first basic organic compound and a compound selected from the group consisting of omeprazol and an alkali salt of omeprazol;
   (b) coating the nucleus with one layer formed by a basic water soluble excipient and a second basic organic compound;
   (c) coating the subcoated nucleus with an enteric coating.

5. An oral pharmaceutical preparation containing omeprazol as active ingredient which comprises:
   (a) a nucleus formed by a mixture of a first basic organic compound and a compound selected from the group consisting of omeprazol and an alkali salt of omeprazol;
   (b) a first coating of said nucleus comprising at least one layer of a basic water soluble excipient and a second basic compound; and
   (c) a second coating formed by an enteric coating;
   wherein said first and second basic compounds are basic optically active or racemic amino acids selected from the group consisting of arginine, histidine, lysine, and tryptophane.

6. An oral pharmaceutical preparation containing omeprazol as active ingredient which comprises:
   (a) a nucleus formed by a mixture of a first basic organic compound and a compound selected from the group consisting of omeprazol and an alkali salt of omeprazol;
   (b) a first coating of said nucleus comprising at least one layer of a basic water soluble excipient and a second basic compound; and
   (c) a second coating formed by an enteric coating;
   wherein said first and second basic compounds comprise physiologically acceptable sodium, lithium, potassium, calcium, magnesium, aluminum or dihydroxyaluminum salts of an amino acid or of a pyridine carboxylic acid.

7. The preparation of claim 6, wherein said amino acid is glycocoll, glutamic acid or lysine.

8. The preparation of claim 6, wherein said pyridine carboxylic acid is nicotinic acid.

9. An oral pharmaceutical preparation containing omeprazol as active ingredient which comprises:
   (a) a nucleus formed by a mixture of a first basic organic compound and a compound selected from the group consisting of omeprazol and an alkali salt of omeprazol;
   (b) a first coating of said nucleus comprising at least one layer of a basic water soluble excipient and a second basic compound; and
   (c) a second coating formed by an enteric coating;
   wherein said first and second basic compounds comprise a physiologically acceptable organic base or a salt thereof with a weak organic or inorganic acid or with a amino acid.

10. The preparation of claim 9, wherein said organic base is guanidine.

11. The preparation of claim 9, wherein said organic base salt is guanidine carbonate, guanidine sodium carbonate, guanidine phosphate, guanidine disodium phosphate, guanidine palmitate, guanidine stearate or guanidine glycocholate.

* * * * *